(12) United States Patent
He et al.

(10) Patent No.: US 7,858,383 B2
(45) Date of Patent: Dec. 28, 2010

(54) CHROMOIONOPHORE AND METHOD OF DETERMINING SODIUM IONS

(75) Inventors: Huarui He, Alpharetta, GA (US); Chao Lin, Alpharetta, GA (US); Neeta Raje, Alpharetta, GA (US); Chusheng Liu, Atlanta, GA (US)

(73) Assignee: Opti Medical Systems, Westbrook, ME (US)

( * ) Notice: Subject to any disclaimer, the term of this patent is extended or adjusted under 35 U.S.C. 154(b) by 686 days.

(21) Appl. No.: 11/743,576

(22) Filed: May 2, 2007

(65) Prior Publication Data

US 2007/0259444 A1 Nov. 8, 2007

Related U.S. Application Data

(60) Provisional application No. 60/796,935, filed on May 3, 2006.

(51) Int. Cl.
G01N 21/75 (2006.01)
(52) U.S. Cl. .................................. 436/166; 540/467
(58) Field of Classification Search .................. None
See application file for complete search history.

(56) References Cited

U.S. PATENT DOCUMENTS

| 4,367,072 A | 1/1983 | Vögtle et al. |
| 4,994,395 A | 2/1991 | Chapoteau et al. |
| 5,011,924 A | 4/1991 | Cram et al. |
| 5,952,491 A | 9/1999 | Leiner et al. |

OTHER PUBLICATIONS

Ingle and Crouch. Spectrochemical Analysis, 1988, p. 2.*
Berry et al., Clin. Chem., 34/11, 1988, 2295-2298.
Helgeson et. al., J.Am. Chem. Soc., vol. 111, 1989, 6339-6350.
Burtis et al. ed. "Tietz Textbook of Clinical chemistry and Molecular Diagnostics" Elsevier Saunders, St. Louis, MO, USA 2006, p. 986-989.
He et al., Anal. Chem. vol. 75, 2003, 449-555.
Gunnlaugsson et al., J. Chem Soc., Perkin Trans.2, 2002, 141-150.

* cited by examiner

*Primary Examiner*—James O Wilson
*Assistant Examiner*—Noble Jarrell
(74) *Attorney, Agent, or Firm*—Gilberto M. Villacorta; Steven M. Reid; Foley & Lardner LLP

(57) ABSTRACT

The invention relates to methods of determining sodium ions in a sample, wherein the ions are contacted with a compound having chromophoric moiety and an ionophoric moiety, where the ionophoric moiety interacts with the sodium ions present in the sample, resulting in the chromophoric moiety changing its radiation absorption properties in the ultraviolet and visible regions of the spectrum. For example, a change in an intensity of an absorption maximum is measured and the ion concentration is determined accordingly.

11 Claims, 3 Drawing Sheets

CHROMOIONOPHORE AND METHOD OF DETERMINING SODIUM IONS

BACKGROUND OF THE INVENTION

The invention relates to chromoionophore comprising an chromophore and an ionophore capable of selectively binding sodium ions for determining sodium ion in a sample. The present invention also relates to a method of determining the concentration of sodium ions in a sample wherein the chromoionophore is contacted with sodium ion in a sample, wherein the intensity of at least one absorption maximum in the visible region changes and the concentration of sodium ion is calculated based on the change in the intensity of the absorption maximum.

The accurate measurement of physiologic cations, such as sodium, potassium, lithium, calcium, and magnesium, is essential in clinical diagnosis. Traditionally, these ions were determined in plasma or serum using ion-selective electrodes (ISE), which are very cumbersome to use and costly to maintain. Serious drawbacks of electrochemical measuring arrangements are the requirement of a reference element, sensitivity towards electrical potentials and electromagnetic interference.

An alternative enzymatic method is based on the activation of β-Galactosidase by cations (Berry et al., *Clin. Chem.*, 34/11, 1988 2295-2298). The high cost and poor stability of the enzyme preclude its extensive application in clinical laboratories. Therefore, the development of practical and inexpensive calorimetric reagents for the clinical determination of these ions in biological fluids remains an important area of research.

U.S. Pat. No. 4,367,072 describes a process for the determination of metal ions using simple crown ethers as ion-binding units. However, the binding is too weak to be useful for many practical applications, such as clinical applications, in which the indicator has to discriminate between ions with very similar properties, e.g., sodium versus potassium or magnesium versus calcium.

U.S. Pat. No. 5,011,924 and U.S. Pat. No. 4,994,395 describe cryptands (or cryptohemispherands) linked with an ionizable chromophore, which changes its color upon binding of ions based on charge interaction between the bound cation and the anion of chromophore. Although all nitrogen atoms in these cryptands are aliphatic, and not electronically conjugated with the chromophore, the results of measurement of serum samples using these chromoionophores are impressive and promising (Helgeson et. al. *J. Am. Chem. Soc.*, vol. 111, 1989, 6339-6350). However, the syntheses of these cryptands, especially of those cryptohemispherands, are lengthy and tedious. Consequently, the manufacturing cost of these reagents remains prohibitively high even in the decades following their discovery. The cost factor could be a reason why these reagents have not replaced those ISE modules in most large clinical analyzers, in which the ISE methods are still dominating (see Burtis et. al. ed. "Tietz Textbook of Clinical chemistry and Molecular Diagnostics" Elsevier Sauders, St. Louis, Mo., USA 2006, page 986).

U.S. Pat. No. 5,952,491 report sodium ionophore, which has π-electron conjugated nitrogen and is coupled to a fluorophore to make luminophore-ionophore sensors where the respective ions are detected by measuring luminescence emission. All three ionophores has been proven to be very effective in determination of sodium in whole blood in which sodium is the major cation. (see He et. al. *Anal. Chem.* Vol. 75, 2003, 449-555), thus showing that the ionophore is effective under physiological conditions.

By coupling to a chromophoric moiety, the ionophore can be converted into colorimetric sensors. The chromophoric moieties can be a nitro-substituted styryl or phenylazo, substituted thiazolevinyl or thiazoleazo, substituted naphthothiazolevinyl or naphthothiazoleazo, substituted naphthylvinyl or naphthylazo, substituted quinolinovinyl or quinolinoazo and their quartemized salts. To date, there has been no systematic investigation of these types of colorimetric reagents. Gunnlaugsson et al. (*J. Chem Soc., Perkin Trans.* 2, 2002, 141-150) describe use of a sodium ionophore with a nitrophenylazo chromophore. The water solubility of this dye is so poor that one has to use organic solvent to solubilize it. The water solubility can be improved dramatically if a charge is introduced into the dye molecules. The absorption wavelength can be red-shifted by replacing the nitrophenyl with a nitrothiazole or larger chromophore-generating substituent.

The present invention provides sodium chromoionophores that are water soluble and can be reliably used for detection of ions in samples that absorb at wavelengths longer than about 400 nm. Examples of such samples are biological fluids including plasma, serum and urine.

For the chromoionophores of the present invention, the amount of ion present is determined by measuring changes in the intensity of at least one absorption maximum of the chromoionophore upon contacting the chromoionophore with an ion. The measurements are done by using standard centralized instruments, such as ultraviolet-visible spectrometers. A calibration curve for an ion is generated from a series of empirically determined absorption spectra. A calibration curve is useful for at-once determining the concentration of ion in a sample from the measured absorbance.

The chromoionophores of this invention absorb visible light (about 400 nm or greater) with reasonable extinction coefficient, thus avoiding those practical problems associated with variable background absorption from optical components, cuvette polymer materials, and biological samples. Further, the invention is well suited for practice in the determination of sodium ion in the presence of physiological concentrations of other alkali ions.

SUMMARY OF THE INVENTION

In brief, the present invention relates to novel chromoionophores, comprising a chromophoric moiety and an ionophoric moiety. The invention further relates to a method of determining sodium ions in a sample, wherein the ions are contacted with a compound having chromophoric moiety and an ionophoric moiety, where the ionophoric moiety interacts with the sodium ions present in the sample, resulting in the chromophoric moiety changing its radiation absorption properties in the ultraviolet and visible regions of the spectrum. In one embodiment, a change in an intensity of an absorption maximum is measured and the ion concentration is determined accordingly.

In one embodiment, the chromoionophores of the invention comprise an ionophore having one or more chelating moieties that is capable of selectively binding sodium ions and a chromophore having a plurality of conjugated unsaturated bonds. The chromoionophore exhibits at least one absorption maximum having a wavelength in the visible region having a first intensity and wherein the absorption maximum has a second intensity that is different from the first intensity in an amount that is by proportional to the concentration of sodium ion present in a mixture comprising sodium ions and the chromoionophore.

In other embodiments, the chromoionophores of the invention are compounds having the Formula (I)

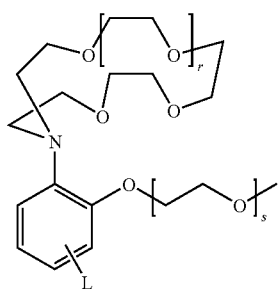

wherein, r and s independently are selected from the group consisting of 0, 1 or 2, and L is a chromophoric moiety. It should be understood that compounds wherein r is 1 and s is 0, and L is

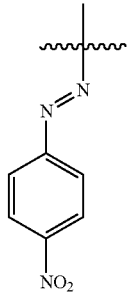

are excluded from the scope of this invention.

The invention further provides a method of determining the concentration of potassium ions in a sample comprising (a) measuring the intensity of at least one absorption maximum of a solution of a chromoionophore sensitive to the presence of sodium ions in solution to obtain a first intensity; wherein the concentration of the chromoionophore in solution is known; and wherein said at least one absorption maximum has a wavelength in the visible region;

(b) contacting the solution of the chromoionophore with the sample; whereby the first intensity changes;

(c) measuring the intensity of at least one absorption maximum to obtain a second intensity;

(d) deriving the concentration of sodium ion in the sample based, in part, on the difference between the first and second intensities.

In one embodiment, at least one absorption maximum occurs at a wavelength that is in the visible region.

In another embodiment, the difference between the first and second intensities results in a colorimetric change in the solution sample comprising the chromoionophore and sodium ions.

In another embodiment, at least one absorption maximum occurs at a wavelength of about 400 nm or greater.

In another embodiment, at least one absorption maximum occurs at a wavelength between about 400 nm and about 800 nm.

DETAILED DESCRIPTION OF THE INVENTION

Figure 1:
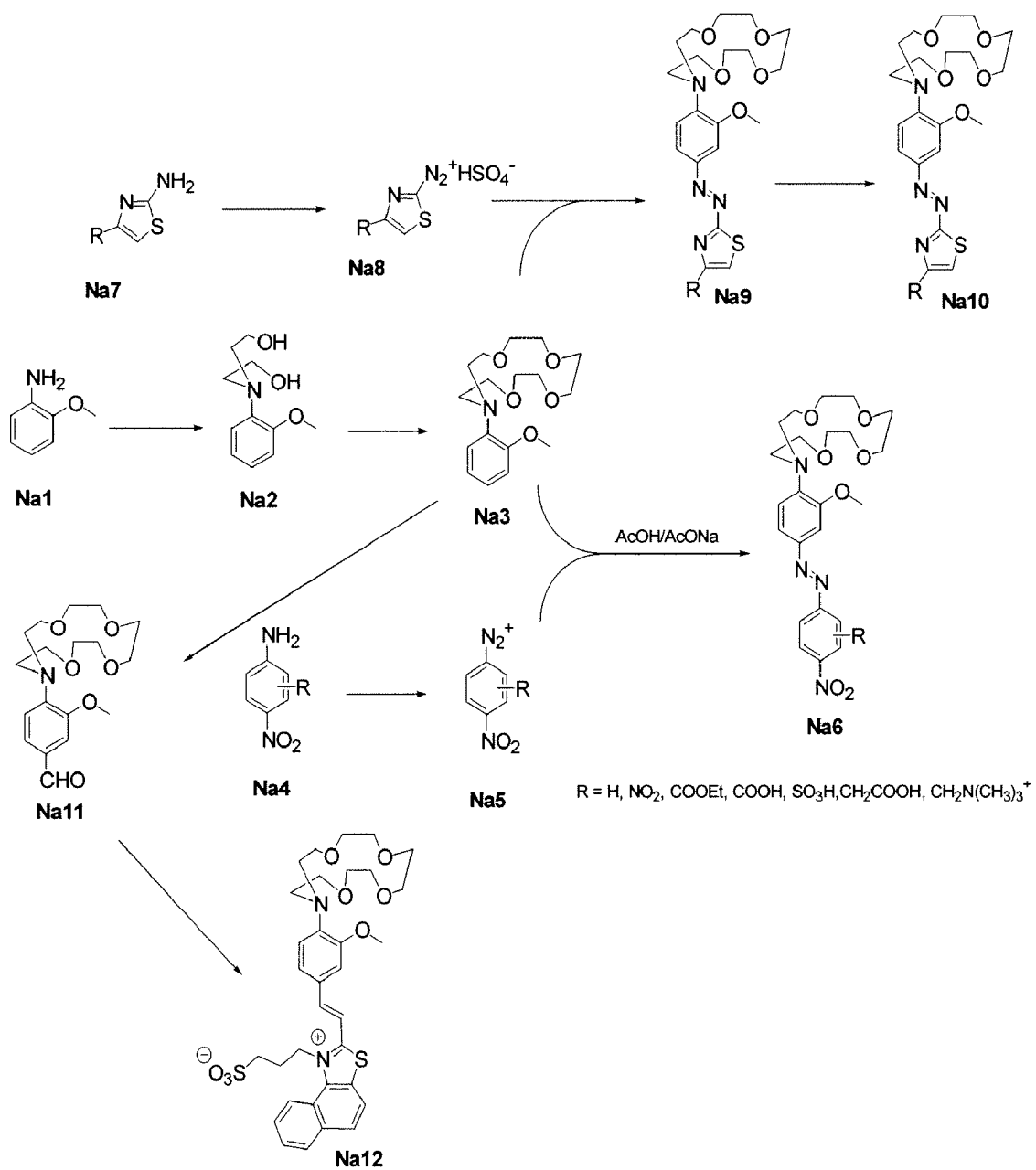
FIG. 1 is an illustration of synthetic pathway to sodium calorimetric indicator.

As used herein, the terms have the following meanings:

The term "alkyl" as used herein refers to a straight or branched chain, saturated hydrocarbon having the indicated number of carbon atoms. For example, ($C_1$-$C_6$) alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents.

The term "alkylene" refers to a divalent alkyl group (e.g., an alkyl group attached to two other moieties, typically as a linking group). Examples of a ($C_1$-$C_7$) alkylene include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH_2CH_2CH_2CH_2CH_2CH_2$—, as well as branched versions thereof. An alkylene group can be unsubstituted or optionally substituted with one or more substituents.

The term "alkoxy" as used herein refers to an —O-alkyl group having the indicated number of carbon atoms. For example, a ($C_1$-$C_6$) alkoxy group includes —O-methyl, —O-ethyl, —O-propyl, —O-iospropyl, —O-butyl, —O-sec-butyl, —O-tert-butyl, —O-pentyl, —O-isopentyl, —O-neopentyl, —O-hexyl, —O-isohexyl, and —O-neohexyl.

The term "alkenyl" as used herein refers to a straight or branched chain unsaturated hydrocarbon having the indicated number of carbon atoms and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents.

The term "Ar" as used herein refers to an aromatic or heteroaromatic moiety. An "aromatic" moiety refers to a 6- to 14-membered monocyclic, bicyclic or tricyclic aromatic hydrocarbon ring system. Examples of an aromatic group include phenyl and naphthyl. An aromatic group can be unsubstituted or optionally substituted with one or more substituents. The term "heteroaromatic" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaromatics are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, naphthothiazolyl, quinoxalinyl. A heteroaromatic group can be unsubstituted or optionally substituted with one or more substituents.

The term "halogen" as used herein refers to —F, —Cl, —Br or —I.

As used herein, the term "heteroatom" is meant to include oxygen (O), nitrogen (N), and sulfur (S).

The term "chromoionophore" as used herein refers to a compound comprising at least one ionophore and at least one chromophore.

The following abbreviations are used herein and have the indicated definitions: LAH is lithium aluminum hydride; DMF is dimethylformamide; NMR is nuclear magnetic resonance; THF is tetrahydrofuran.

Compounds of the Invention

The present invention provides compounds of Formula (I) referred to as "chromoionophores"

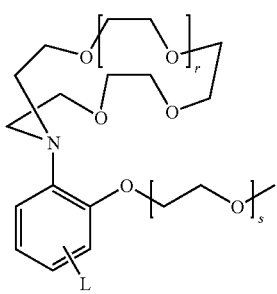

wherein r and s are as defined above.

In one embodiment, the chromophoric moiety L is selected from the group consisting of —NO$_2$, Formula (II) and (III),

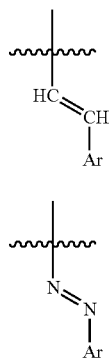

wherein, Ar is a (C$_6$-C$_{10}$) aromatic moiety or a (C$_5$-C$_{14}$) heteroaromatic moiety containing one or more heteroatoms selected from N, O, and S, and wherein Ar is substituted with one or more substituents selected from the group consisting of hydrogen, —NO$_2$, —NO, —CN, (C$_1$-C$_8$) straight chain or branched alkyl, (C$_2$-C$_8$) alkenyl, halogen, —SO$_3$H, —W—COOH, —W—N(R$^1$)$_3$, —C(O)OR$^1$, —C(O)R$^1$; W is (C$_1$-C$_8$) alkylene; and R$^1$ is selected from the group consisting of hydrogen and (C$_1$-C$_8$) straight chain or branched alkyl.

In another embodiment, Ar is selected from the group consisting of Formula (IV), (V), (VI), and (VII)

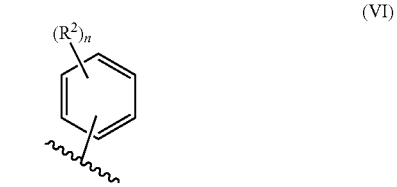

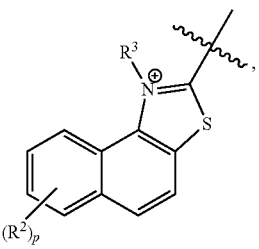

wherein X is O or S, and Y is N or C;

R$^2$, at each occurrence, is independently selected from the group consisting of hydrogen, —NO$_2$, —NO, —CN, C$_1$-C$_8$ straight chain or branched alkyl, (C$_2$-C$_8$) alkenyl, halogen, —SO$_3$H, -Q-COOH, -Q-N(R$^4$)$_3$, —C(O)OR$^4$, —C(O)R$^4$.

R$^3$ is -Q-SO$_3^-$ or -Q-COO$^-$.

Q is (C$_1$-C$_8$) alkylene.

R$^4$ is selected from the group consisting of hydrogen and (C$_1$-C$_8$) straight chain or branched alkyl;

Variable l is an integer selected from 1 to 3; m is an integer selected from 1 to 7; n is an integer selected from 1 to 5; and p is an integer selected from 1 to 6.

Specific examples of compounds of Formula I are provided below:

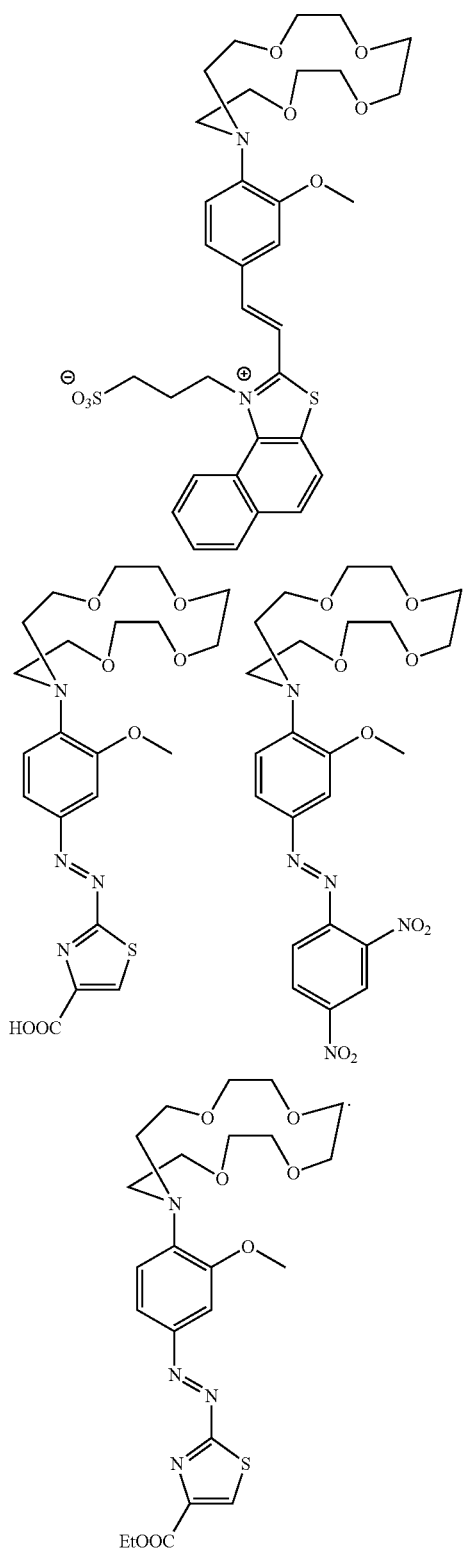

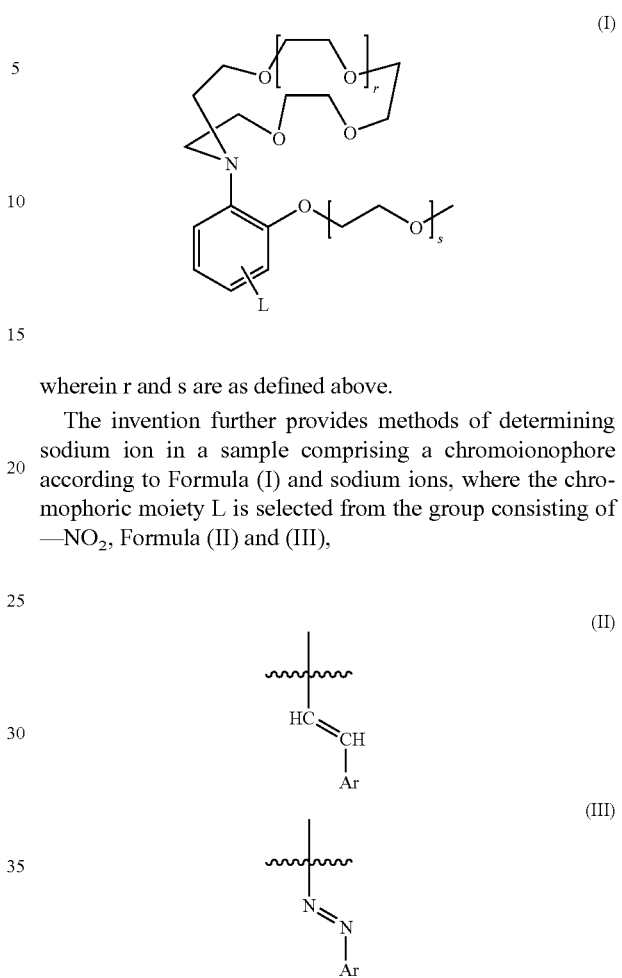

wherein r and s are as defined above.

The invention further provides methods of determining sodium ion in a sample comprising a chromoionophore according to Formula (I) and sodium ions, where the chromophoric moiety L is selected from the group consisting of —NO$_2$, Formula (II) and (III), $$\text{(II)}$$

$$\text{(III)}$$

wherein, Ar is a ($C_6$-$C_{10}$) aromatic moiety or a ($C_5$-$C_{14}$) heteroaromatic moiety containing one or more heteroatoms selected from N, O, and S, and wherein Ar is substituted with one or more substituents selected from the group consisting of hydrogen, —NO$_2$, —NO, —CN, ($C_1$-$C_8$) straight chain or branched alkyl, ($C_2$-$C_8$) alkenyl, halogen, —SO$_3$H, —W—COOH, —W—N(R$^1$)$_3$, —C(O)OR$^1$, —C(O)R$^1$; W is ($C_1$-$C_8$) alkylene; and R$^1$ is selected from the group consisting of hydrogen and ($C_1$-$C_8$) straight chain or branched alkyl.

The invention further provides methods of determining sodium ion in a sample comprising a chromoionophore according to Formula (I) and sodium ions, where Ar is selected from the group consisting of Formula (IV), (V), (VI), and (VII)

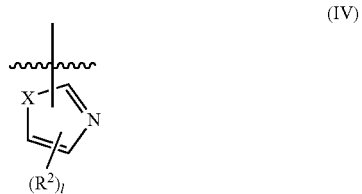

The invention further provides methods of determining sodium ion in a sample comprising a chromoionophore according to Formula (I) and sodium ions, where the chromoionophore has the general Formula (I)

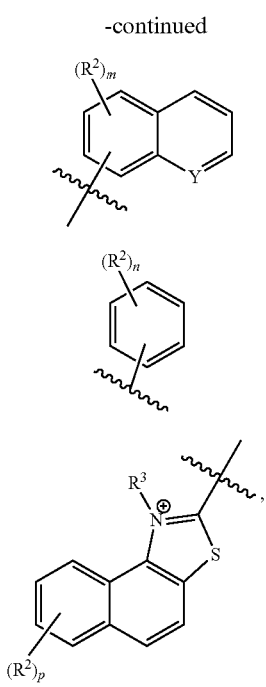

wherein X is O or S, and Y is N or C;

R², at each occurrence, is independently selected from the group consisting of hydrogen, —NO₂, —NO, —CN, $C_1$-$C_8$ straight chain or branched alkyl, ($C_2$-$C_8$) alkenyl, halogen, —SO₃H, -Q-COOH, -Q-N(R⁴)₃, —C(O)OR⁴, —C(O)R⁴.

R³ is -Q-SO₃⁻ or -Q-COO⁻.

Q is ($C_3$-$C_8$) alkylene.

R⁴ is selected from the group consisting of hydrogen and ($C_1$-$C_8$) straight chain or branched alkyl.

Variable l is an integer selected from 1 to 3; m is an integer selected from 1 to 7; n is an integer selected from 1 to 5; and p is an integer selected from 1 to 6.

The invention further provides methods of determining sodium ion in a sample comprising a chromoionophore according to Formula (I) and sodium ions, where the sample is a biological fluid. Examples of biological fluids are whole blood, plasma, serum, and urine.

The invention further provides methods of determining sodium ion in a sample comprising a chromoionophore according to Formula (I) and sodium ions, where the sample has a pH of 6.5 or above.

Preparation of the Compounds of Formula (I)

Those skilled in the art will recognize that there are a variety of methods available to synthesize molecules described herein. The synthesis of the chromoionophore (Na6) and (Na12) from commercially available compounds is illustrated in FIG. 1. o-Anisidine (Na1) was di-alkylated with 2-chloroethanol then reacted with bis[(2-chloro-ethoxy)] ethane. The resultant phenylazacrown ether (Na3) was coupled with diazonium (Na5) to afford chromoionophore (Na6). Na3 was also converted to (Na12).

Example 1

N,N-Bis(2-hydroxyethyl)-2-methoxyaniline (Na2). Na1 (452 g, 4 mol) was dissolved in 2-chloroethanol (1,932 g, 24 mol) and heated to 80° C. for 15 min. K₂CO₃ (608 g, 4.4 mol) was slowly added such that the temperature of this exothermic reaction was kept below 110° C. The mixture was heated at 95° C. for 22 h., cooled and approximately 800 mL of unreacted 2-chloroethanol was removed under vacuum. The residue was diluted with water (1 L) and extracted with CHCl₃ (2×1 L). The CHCl₃ solutions were back-washed with water (5×1.5 L), dried over K₂CO₃ and the solvent evaporated to afford 404 g (48%) of a light brown oil. ¹H NMR (CDCl₃): δ=3.18 (t, 4H), 3.50 (t, 4H), 3.60 (m, 2H), 3.82 (s, 3H), 6.90 (m, 2H), 7.10 (m, 1H), 7.19 (m, 1H). Anal. Calcd. for C₁₁H₁₇NO₃: C, 62.54; H, 8.11; N, 6.63. Found: C, 61.33; H, 8.28; N, 6.43.

Example 2

2-Methoxyphenylaza-15-crown-5 (Na3). Na2 (403 g, 1.91 mol) was dissolved in dioxane (2.21 L) and heated at 80° C. for 20 min. Powdered NaOH (168 g, 4.20 mol) was added slowly within about 3 h. The temperature was then increased to 95° C., bis(2-chloroethanoxyethane) (300 mL, 1.93 mol) added in one portion and the mixture kept at 95° C. for 30 h. The suspension was then filtered hot, the solvent evaporated, and the residue treated with a solution of NaClO₄ (234 g, 1.91 mol) in methanol (640 mL). The mixture was stirred at 60° C. for 30 min and concentrated to about 300 mL. Ethyl acetate (860 mL) was added, the mixture stirred at room temperature for 20 min then allowed to stand at room temperature for 2 h. The resulted precipitate was filtered, washed with ethyl acetate (2×200 mL) and dried at room temperature for 30 min to give 199 g of azacrown-sodium perchlorate complex as a soft white powder. This powder was dissolved in a mixture of CH₂Cl₂ (600 mL) and water (600 mL), the layers separated and the aqueous phase was extracted with CH₂Cl₂ (400 mL). The organic solutions were combined, washed with water (8×600 mL), dried over Na₂SO₄ then evaporated to afford 100.4 g (16%) of pale yellow oil. ¹NMR (CDCl₃) δ=3.49 (t, 4H), 3.68 (t, 16H), 3.82 (s, 3H), 6.88 (m, 3H), 7.12 (m, 1H). Anal. Calcd for C₁₇H₂₇NO₅: C, 62.70; H, 8.36; N, 4.30. Found: C, 61.63; H, 8.44; N, 4.26.

Example 3

4-(2',4'-Dinitrophenylazo)-2-methoxyphenylaza-15-crown-5 (Na6, R=NO₂). Na3 (1.62 g, 5 mmol) was dissolved in 50 mL tetrahydrofuran and the resulting solution was diluted with 50 mL methanol. To this solution 2.54 g (10 mmol) 2,4-dinitrophenyldiazonium tetrafluoroborate was added in three portions. The suspension was stirred at room temperature for 2 hours. When TLC showed that Na3 was gone, the solvent was evaporated and the residue was dissolved in 500 mL chloroform, washed 500 mL water. The solvent was evaporated to get about 3.32 g oily gum. This crude product was purified with a short column, packed with 25 g silica gel, eluted with chloroform to remove front impurities, then using chloroform/methanol (99/1, v/v) to get 0.84 g dark red gum product. ¹H NMR (CDCl₃) 3.60 (t, 16H), δ=3.70 (t, 4H), 3.82 (s, 3H), 6.78 (d, 1H), 7.36 (d, 1H), 7.52 (m, 1H), 8.22 (d, 2H), 8.80 (s, 1H).

Example 4

Synthesis of Na8 (R=CH₂COOEt). Under the cooling of ice-water bath, sodium nitride 1.39 g (20 mmol) was added to 16 g (40.8 mmol) concentrated sulfuric acid and stood for five minutes, then warmed to 60° C., the solution became clear. The solution was cooled to under 0° C. with ice-salt bath; then 3.72 g (20 mmol) ethyl 2-aminothiazole-4-acetate was added in one portion. The solution was kept at under 0° C. and stirred for two hours. KI-starch paper monitored the free nitrous acid until reaction completed. Used immediately for next step.

Example 5

Synthesis of Na9 (R=CH$_2$COOEt). Under the cooling of ice-water, the solution of Na8 was slowly transferred into the solution of Na3 (4.87 g (3 mmol) and sodium acetate 8.10 g (82 mmol) in 50 mL acetic acid. The resulting suspension mixture was stirred overnight and poured into stirring 400 mL DI water, extracted with 200 mL chloroform. The organic layer was washed with 200 mL sat. sodium carbonate, 200 mL DI water, dried over anhydrous sodium sulfate. The solvent was evaporated and the residue was further purified with 10 g silica gel 60 using chloroform:methanol 9:1 (v/v) as elution to afford 2.53 g dark red product. $^1$H NMR (CDCl$_3$) 1.25 (t, 3H), 3.60 (t, 16H), δ=3.70 (t, 4H), 3.82 (s, 3H), 4.20 (q, 2H), 6.75 (d, 1H), 7.35 (d, 1H), 7.48 (m, 1H), 8.20 (s, 1H).

Example 6

Synthesis of Na10 (R=CH$_2$COOH). To a solution of 2.50 g Na9 in 50 mL methanol was added 10 mL water and 10 mL 1 N KOH. The resulting solution was warmed to 60° C. and let it cooled to room temperature for 1 h. The solvent was evaporated and the residue was dissolved in 5 mL methanol. This solution was directly used as stock solution.

Example 7

Synthesis of Na11. Na3 (100 g, 308 mmol) was dissolved in DMF (145 mL, 1850 mmol) in a 500 mL three-neck flask and cooled to −5° C. POCl$_3$ (57.4 mL, 616 mmol) was added dropwise via an addition funnel such that the solution temperature did not exceed 5° C. After stirring at room temperature for 16 h, the solution was heated to 60° C. for 1 h, cooled, poured into 500 g ice, the flask rinsed flask with 70 mL water, and the combined aqueous solutions adjusted to pH 7 (by pH paper) with saturated K$_2$CO$_3$. The solution was extracted with CHCl$_3$ (2×500 mL), the CHCl$_3$ phase washed with water (2×500 mL) then dried over MgSO$_4$ (100 g) for 1 h. Evaporation of the solvent afforded 85 g light yellow oil that crystallized upon standing overnight. Re-crystallization from ethyl acetate/hexane (1:4) afforded 56 g (51%) light orange crystals. $^1$H NMR (CDCl$_3$) δ=3.68 (t, 16H), 3.78 (t, 4H), 3.82 (s, 3H), 7.05 (m, 1H), 7.28 (m, 2H), 9.78 (s, 1H). Anal. Calcd for C$_{18}$H$_{27}$NO$_6$: C, 61.17; H, 7.70; N, 3.96. Found: C, 61.05; H, 8.01; N, 4.04.

Example 8

Synthesis of Na12. Na11 (0.35 g, 1 mmol) was dissolved in 10 mL 10 mL ethanol. To this solution 0.35 g (1.1 mmol) 2-methyl-1-(3-sulfopropyl)naphtho[1,2-d]thiazolium inner salts and 0.11 g (1.1 mmol) triethylamine were added. The resulting solution was stirred under reflux for 18 h. after cooling. The solvent was evaporated and the residue was purified by a silica gel column with CHCl3/methanol (99/1, v/v) as eluent to give 0.48 g dark brown powder. $^1$H NMR (CDCl$_3$) δ=2.1 (m, 2H), 3.45 (m, 4H) 3.68 (t, 16H), 3.78 (t, 4H), 3.82 (s, 3H), 6.9-8.3 (m, 9H).

Example 9

Figure 2:
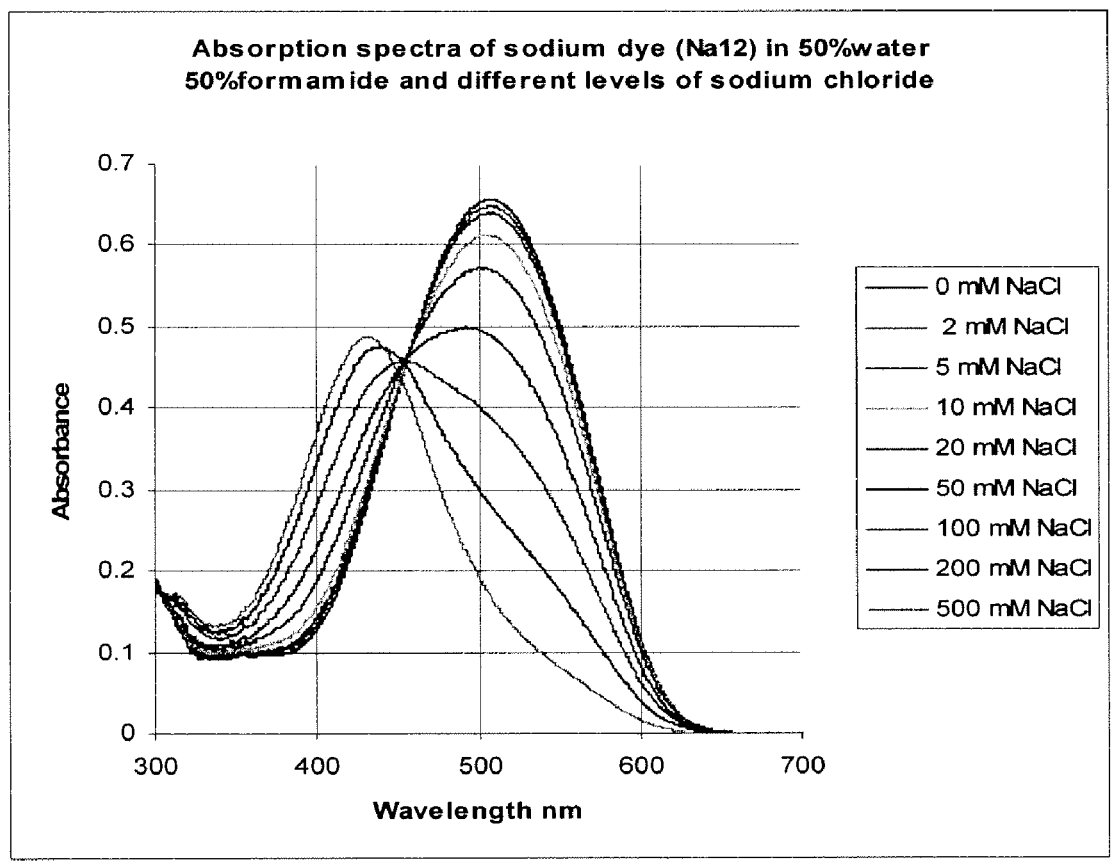
FIG. 2 is a graph illustrating the absorbance of a sodium colorimetric indicator in accordance with the invention versus sodium concentration in serum sample.

Method of Determining Sodium Ions: Solvents and reagents are purchased from Aldrich (Milwaukee, Wis.) and used without further purification. Analytical grade buffer and inorganic salts are purchased from either Fluka AG (Buchs, Switzerland) or Sigma Co. (St. Louis, Mo.). Absorption measurements are performed with a Shimadzu UV2101PC spectrophotometer equipped with a jacketed cuvette holder for controlling of temperature. Titration of a chromoinophore is carried out in the following manner: A methanolic solution of a chromoionophore is diluted with buffer, deionized water or deionized water with organic co-solvent in a volumetric flask to make about 30 μM final solution, the required amount of solid salt is added and the solution's absorption spectrum is measured. The typical titration spectra are shown in FIG. 2.

Figure 3:
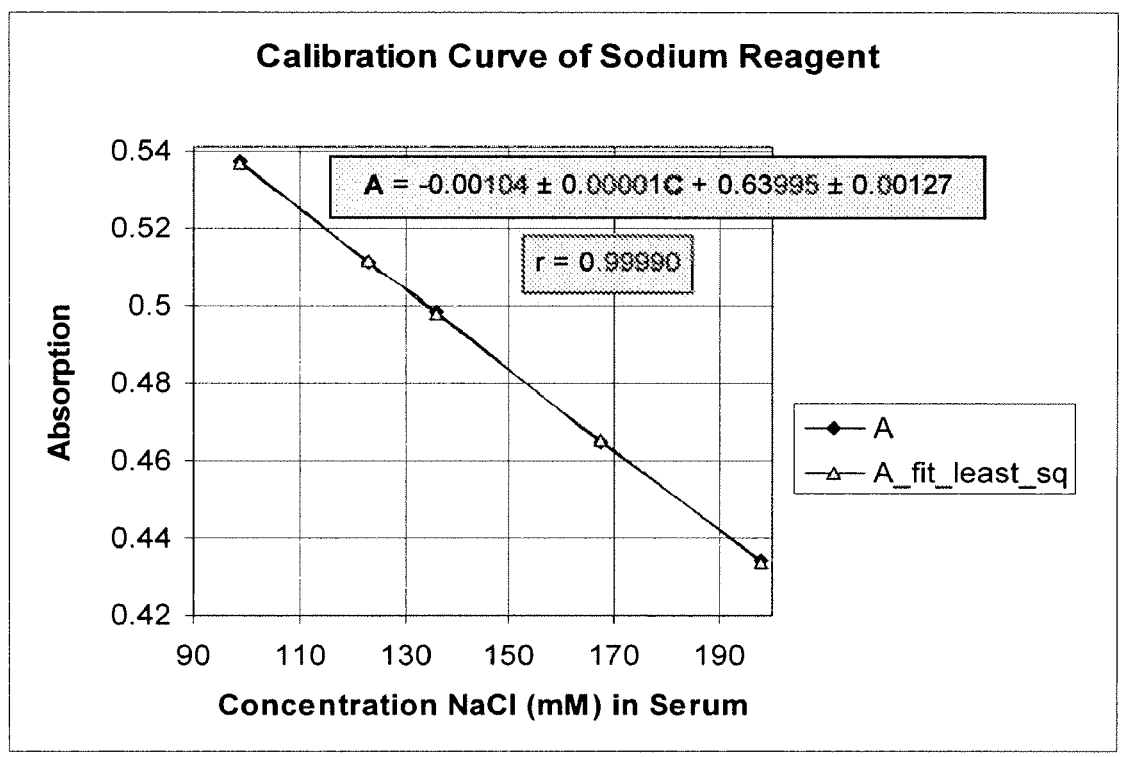
FIG. 3 is a graph illustrating a calibration curve a sodium calorimetric indicator in accordance with the invention versus sodium concentration in serum sample.

A sodium colorimetric reagent used for FIG. 3 is formulated as follows: a methanolic solution containing of about 2.3 mg of calorimetric sodium indicator Na10 (R=CH$_2$COOH) is mixed with 0.905 g tetramethylammonium hydroxide pentahydrate and 0.0292 g ethylenediaminetetraacetic acid. The resulting mixture is dissolved in methanol and bring the total volume to 100 ml. 2.7 ml of this solution is mixed with 0.3 ml serum or aqueous sample, incubated at 37° C. for 5 min. The absorption values are recorded at wavelength of 486 nm, and are used to plot the chart shown in FIG. 3.

What is claimed is:

1. A chromoionophore of Formula (I)

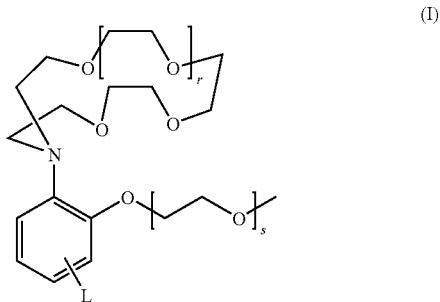

wherein,
r and s independently are selected from the group consisting of 0, 1 or 2, and
L is a chromophoric moiety selected from the group consisting of —NO$_2$, Formula (II) and (III),

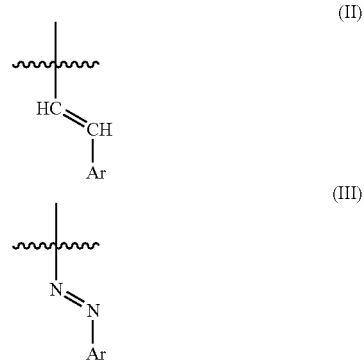

wherein
Ar is (C$_6$-C$_{10}$) aromatic moiety or a (C$_5$-C$_{14}$) heteroaromatic moiety containing one or more heteroatoms selected from N, O, and S, and wherein Ar is substituted with one or more substituents selected from the group consisting of hydrogen, —NO$_2$, —NO, —CN, (C$_1$-C$_8$)

straight chain or branched alkyl, (C₂-C₈) alkenyl, halogen, —SO₃H, —W—COOH, —W—N(R¹)₃, —C(O)OR¹, and —C(O)R¹;

W is (C₁-C₈) alkylene; and

R¹ is selected from the group consisting of hydrogen and (C₁-C₈) straight chain or branched alkyl, with the proviso that when r is 1 and s is 0, then L is not

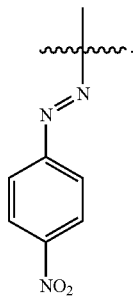

2. The chromoionophore according to claim 1, wherein Ar is selected from the group consisting of Formula (IV), (V), (VI), and (VII)

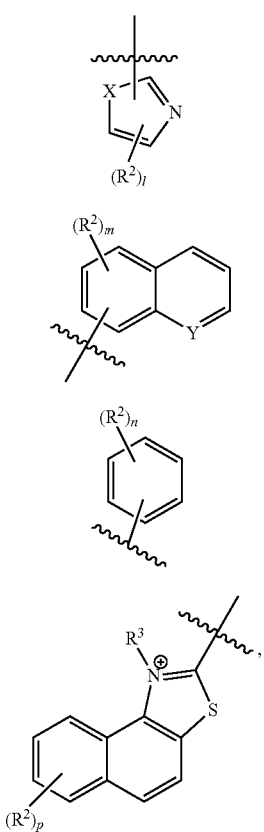

wherein

X is O or S;

Y is N or C;

R², at each occurrence, is independently selected from the group consisting of hydrogen, —NO₂, —NO, —CN, $C_1$-$C_8$ straight chain or branched alkyl, (C₂-C₈) alkenyl, halogen, —SO₃H, -Q-COOH, -Q-N(R⁴)₃, —C(O)OR⁴, and —C(O)R⁴;

R³ is -Q-SO₃⁻ or -Q-COO⁻;

Q is (C₁-C₈) alkylene;

R⁴ is selected from the group consisting of hydrogen and (C₁-C₈) straight chain or branched alkyl;

l is an integer selected from 1 to 3;

m is an integer selected from 1 to 7;

n is an integer selected from 1 to 5; and p is an integer selected from 1 to 6.

3. The chromoionophore according to claim 1, wherein the chromoionophore is selected from the group consisting of

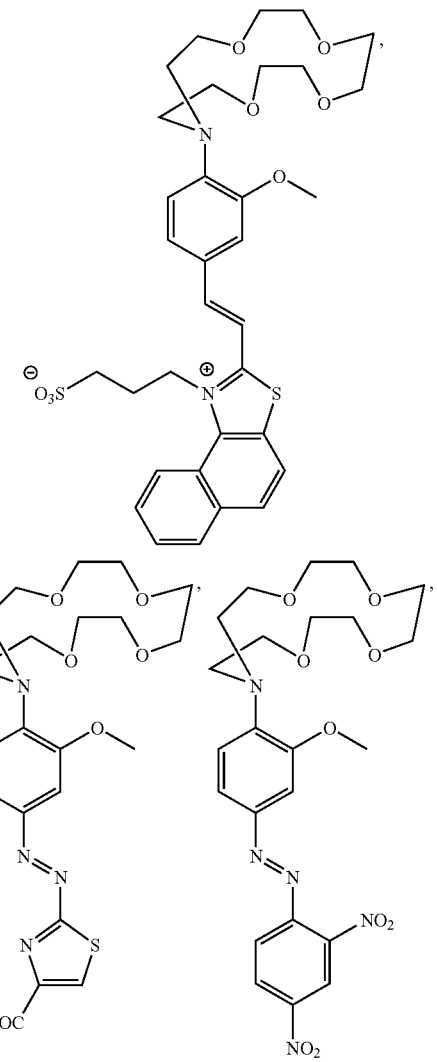

-continued

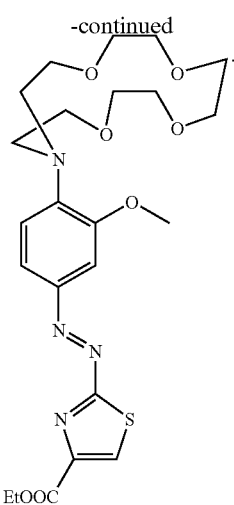

4. A method of determining the concentration of sodium ions in a sample comprising
   (a) measuring the intensity of at least one absorption maximum of a solution of a chromoionophore of Formula (I)

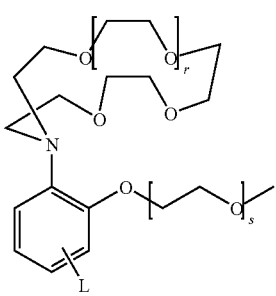
(I)

wherein
r and s independently are selected from the group consisting of 0, 1 or 2, and
L is a chromophoric moiety selected from the group consisting of —$NO_2$, Formula (II) and (III), (II)

(III)

wherein,
Ar is a ($C_6$-$C_{10}$) aromatic moiety or a ($C_5$-$C_{14}$) heteroaromatic moiety containing one or more heteroatoms selected from N, O, and S, and wherein Ar is substituted with one or more substituents selected from the group consisting of hydrogen, —$NO_2$, —NO, —CN, ($C_1$-$C_8$) straight chain or branched alkyl, ($C_2$-$C_8$) alkenyl, halogen, —$SO_3H$, —W—COOH, —W—N($R^1$)$_3$, —C(O)OR$^1$, and —C(O)R$^1$;
W is ($C_1$-$C_8$) alkylene; and
$R^1$ is selected from the group consisting of hydrogen and ($C_1$-$C_8$) straight chain or branched alkyl,
with the proviso that when r is 1 and s is 0, then L is not

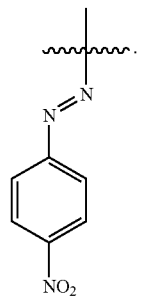

and sensitive to the presence of sodium ions in solution to obtain a first intensity; wherein the concentration of the chromoionophore in solution is known; and
wherein said at least one absorption maximum has a wavelength in the visible region;
   (b) contacting the solution of the chromoionophore with the sample; whereby the first intensity changes;
   (c) measuring the intensity of at least one absorption maximum to obtain a second intensity;
   (d) deriving the concentration of sodium ion in the sample based, in part, on the difference between the first and second intensities.

5. The method according to claim 4, wherein at least one absorption maximum occurs at a wavelength of about 400 nm or greater.

6. The method according to claim 4, wherein at least one absorption maximum occurs at a wavelength between about 400 nm and about 800 nm.

7. The method according to claim 4, wherein Ar is selected from the group consisting of Formula (IV), (V), (VI), and (VII)

(IV)

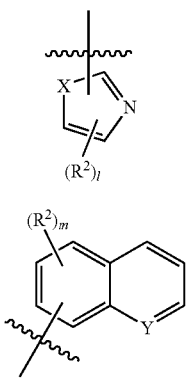

(V)

-continued

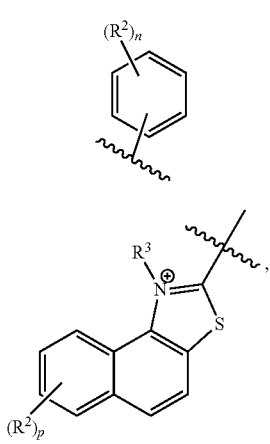

wherein
X is O or S;
Y is N or C;
R² , at each occurrence, is independently selected from the group consisting of hydrogen, —NO₂, —NO, —CN, $C_1$-$C_8$ straight chain or branched alkyl, ($C_2$-$C_8$) alkenyl, halogen, —SO₃H, -Q-COOH, -Q-N(R⁴)₃, —C(O)OR⁴, and —C(O)R⁴;
R³ is -Q-SO₃⁻ or -Q-COO⁻;
Q is ($C_1$-$C_8$) alkylene;
R⁴ is selected from the group consisting of hydrogen and ($C_1$-$C_8$) straight chain or branched alkyl;
l is an integer selected from 1 to 3;
m is an integer selected from 1 to 7;
n is an integer selected from 1 to 5; and
p is an integer selected from 1 to 6.

8. The method according to claim 4, wherein the chromoionophore is selected from the group consisting of

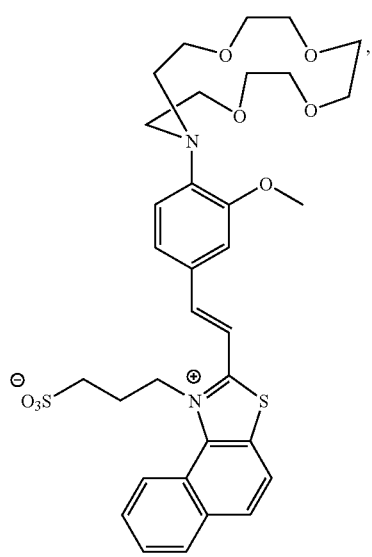

-continued

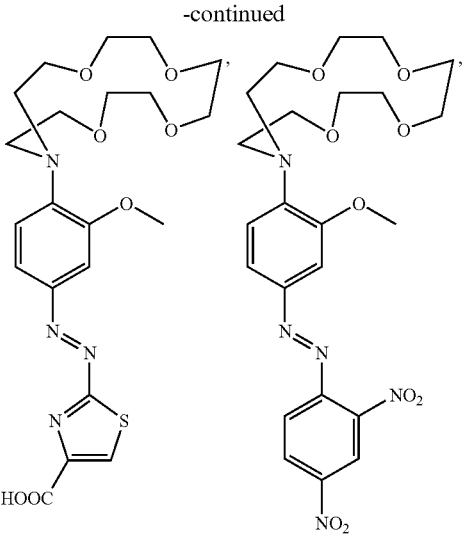

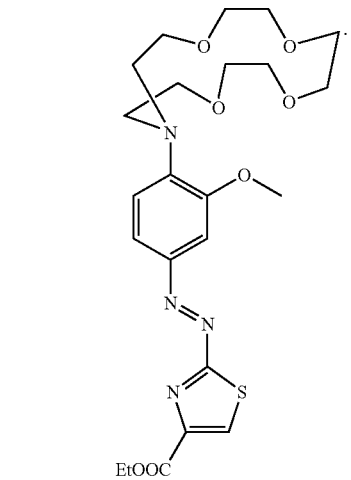

9. The method according to claim 4, wherein the sample is a biological fluid.

10. The method according to claim 9, wherein the biological fluid is selected from the group consisting of whole blood, plasma, serum, and urine.

11. The method according to claim 4, wherein the sample has a pH of 6.5 or above.

* * * * *